United States Patent [19]

Mukai et al.

[11] Patent Number: 4,960,886
[45] Date of Patent: Oct. 2, 1990

[54] CHARGE TRANSFER COMPLEX FORMED BETWEEN BENZOQUINONE DERIVATIVE AND ELECTRON DONOR AND PROCESS FOR PRODUCING THE SAME

[75] Inventors: Toshio Mukai; Yoshiro Yamashita; Takanori Suzuki, all of Miyagi, Japan

[73] Assignees: Fuji Xerox Co., Ltd., Tokyo; Toshio Mukai, Miyagi, both of Japan

[21] Appl. No.: 131,665

[22] Filed: Dec. 11, 1987

[30] Foreign Application Priority Data

Dec. 15, 1986 [JP] Japan .................................. 61-298371
Dec. 15, 1986 [JP] Japan .................................. 61-298372
Dec. 15, 1986 [JP] Japan .................................. 61-298373

[51] Int. Cl.$^5$ .................. C07D 279/18; C07D 327/04
[52] U.S. Cl. ........................................ 544/35; 549/30; 549/31; 549/17; 549/15; 549/32; 549/44; 548/440; 546/121; 544/347; 544/344
[58] Field of Search ........................ 549/30, 31, 17, 15, 549/32, 44; 548/440; 546/121; 544/347, 344, 35

[56] References Cited

U.S. PATENT DOCUMENTS

| | | | |
|---|---|---|---|
| 3,403,165 | 9/1968 | Matsunaga | 549/31 |
| 4,384,025 | 5/1983 | Hilti et al. | 549/31 |
| 4,465,845 | 8/1984 | Okamoto et al. | 549/30 |
| 4,505,858 | 3/1985 | Mayer | 549/31 |
| 4,578,220 | 3/1980 | Huenig et al. | 549/30 |
| 4,617,151 | 10/1986 | Mayer et al. | 549/31 |

FOREIGN PATENT DOCUMENTS

| | | | |
|---|---|---|---|
| 3150273 | 6/1988 | Japan | 549/31 |
| 3150274 | 6/1988 | Japan | 549/31 |
| 3225382 | 9/1988 | Japan | 549/31 |
| 0738338 | 6/1981 | U.S.S.R. | 549/31 |

OTHER PUBLICATIONS

Chemical Abstracts; vol. 88(9):62375b, 1977.
Summary of Presentation distributed on Jul. 21, 1986 at the 8th Organic Chemistry Colloquium in Japan entitled: "Novel Electron Acceptor Having Fused Heterocyclic Rings" by Yoshiro Yamashita.

*Primary Examiner*—Patrick P. Garvin
*Assistant Examiner*—E. D. Irzinsci
*Attorney, Agent, or Firm*—Finnegan, Henderson, Farabow, Garrett, and Dunner

[57] ABSTRACT

A charge transfer complex formed between a benzoquinone derivative represented by formula

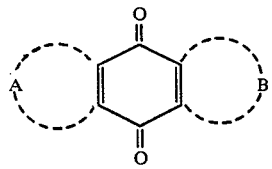

wherein at least one of the rings A and B represents a heterocyclic ring as defined in the specification, and an electron donor, and a salt of an anion or anion radical of the benzoquinone derivative of the above formula are disclosed. The charge transfer complex and the salt are useful as electronic materials.

9 Claims, No Drawings

CHARGE TRANSFER COMPLEX FORMED BETWEEN BENZOQUINONE DERIVATIVE AND ELECTRON DONOR AND PROCESS FOR PRODUCING THE SAME

FIELD OF THE INVENTION

This invention relates to a charge transfer complex useful as an organic electrophotographic material and a process for producing the charge transfer complex, a salt of an anion or anion radical of a benzoquinone derivative useful as an organic electrophotographic material and a process for preparing the anion or anion radical, and a novel benzoquinone derivative useful for producing the charge transfer complex or the anion or anion radical salt and a process for preparing the benzoquino derivative.

BACKGROUND OF THE INVENTION

Known compounds useful as organic electronic materials, such as organic semi-conductors, include tetracyanoanthraquinodimethane and derivatives thereof as disclosed, e.g., in Japanese Patent Application (OPI) Nos. 149259/82 and 55450/83, etc.

The tetracyanoanthraquinodimethane compounds have a basic skeleton represented by the following formula

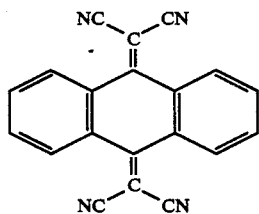

with various substituents being bonded thereto.

These tetracyanoanthraquinodimethane compounds are synthesized from the corresponding anthraquinone compounds and are useful as organic electronic materials, such as organic semi-conductors, organic photographic materials, organic conductors, thermistors, and the like.

The inventors previously succeeded to isolate a charge transfer complex composed of the above-described tetracyanoquinodimethane compound and an electron donating compound at room temperature as a pure solid and found that the resulting charge transfer complex is more useful as an organic electronic material than the tetracyanoquinodimethane compounds per se. They also found that compounds derived from the tetracyanoanthraquinodimethane compounds by displacing at least one of the two benzene condensed rings thereof with other heterocyclic ring and modifying the two dicyanomethylene groups thereof with various groups are also useful as organic electronic materials well, as disclosed in Japanese Patent Application (OPI) Nos. 33157/87 and 32465/87 (the term "OPI" means an unexamined and published patent application).

SUMMARY OF THE INVENTION

The inventors have conducted further researches into analogous compounds of the above-described tetracyanoquinodimethane compounds useful as a starting material for charge transfer complexes. As a result, it has now been found that a specific benzoquinone derivative including a novel compound provides a novel charge transfer complex which is useful as an organic electronic material. It has further been found that a salt of an anion or anion radical of the benzoquinone derivative is also useful as an organic electronic material.

Accordingly, one object of this invention is to provide a novel charge transfer complex formed between a benzoquinone derivative and an electron donor.

Another object of this invention is to provide a process for producing the charge transfer complex.

A still another object of this invention is to provide a salt of an anion or anion radical of a benzoquinone derivative, which is useful as an organic electronic material.

A further object of this invention is to provide a process for preparing the salt of a benzoquinone derivative.

A still further object of this invention is to provide a novel benzoquinone derivative, which is useful as a starting material for producing the above-described charge transfer complex.

A yet further object of this invention is to provide a process for preparing the novel benzoquinone derivative.

That is, the present invention provides a charge transfer complex formed between a benzoquinone derivative represented by formula (I)

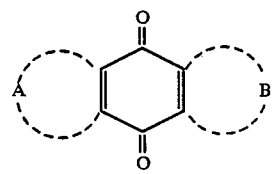

wherein one of

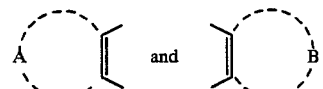

represents a heterocyclic ring selected from

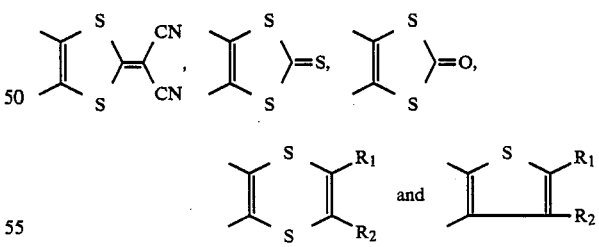

and the other represents one of the heterocyclic ring or a group of formula

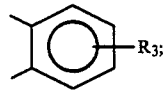

$R_1$, $R_2$, and $R_3$ each represents a hydrogen atom, an alkyl group, an aryl group, an aralkyl group, an alkoxy group, a halogen atom, a nitro group, a cyano group, or a carboxylic ester group, and an electron donor, and a process for producing the same.

The present invention further provides a salt of an anion or anion radical of the benzoquinone derivative represented by formula (I), and a process for producing the same, which comprises reacting the benzoquinone derivative of formula (I) with a metal iodide and, if desired, subjecting the product to salt exchange reaction with a cationic compound.

The present invention furthermore relates to a novel benzoquinone derivative represented by the formula

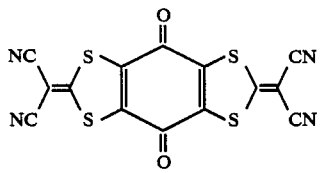

and a process for producing the same, which comprises oxidizing a hydroquinone derivative represented by formula (II)

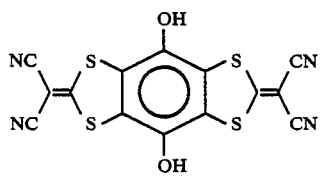

(II)

with an oxidizing agent.

DETAILED DESCRIPTION OF THE INVENTION

In formula (I), preferred examples of the heterocyclic ring include

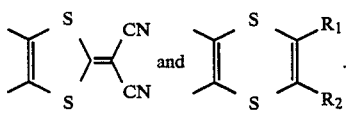

The alkyl, aralkyl, alkoxy, and carboxylic acid ester group represented by $R_1$, $R_2$ and $R_3$ preferably have up to 20 carbon atoms. Examples of the aryl group represented by $R_1$, $R_2$ and $R_3$ include a phenyl group and a naphthyl group, which may be substituted with a substituent having 1 to 20 carbon atoms or may be condensed with a heterocyclic ring. Examples of the halogen atom for $R_1$, $R_2$ and $R_3$ include a fluorine atom, a bromine atom, a chlorine atom and an iodine atom, with a fluorine atom, a bromine atom and a chlorine atom being preferred. In particular, a cyano group is preferred for $R_1$, $R_2$ and $R_3$ among others.

Specific examples of the benzoquinone derivative represented by formula (I) are shown below. Abbreviations of Compounds (1) to (5) are in the parentheses.

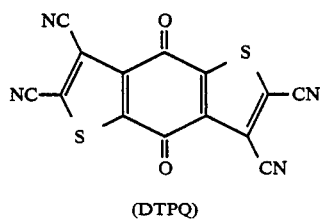

(DTPQ)

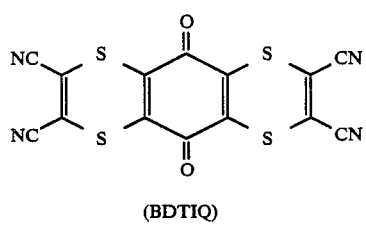

(BDTIQ)

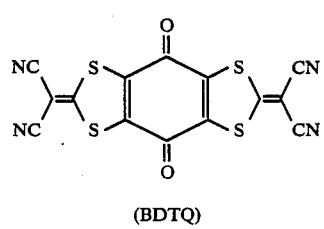

(BDTQ)

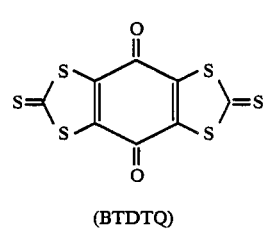

(BTDTQ)

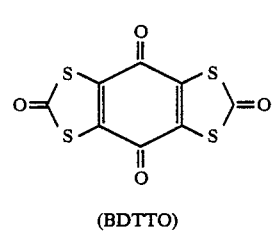

(BDTTO)

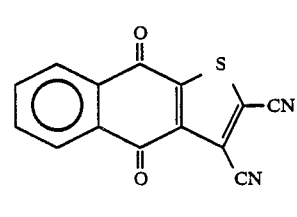

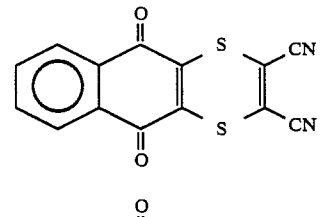

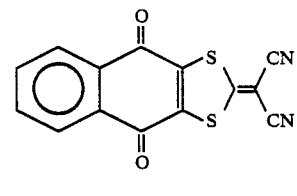

-continued

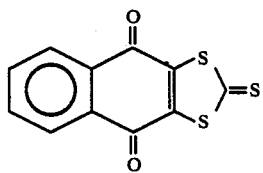  (9)

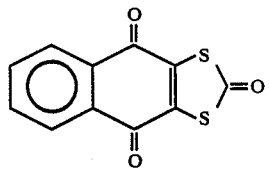  (10)

Of these compounds, Compound (3) is a novel compound.

Process for preparing the benzoquinone derivatives represented by formula (I) other than Compound (3) are shown below together with publications to be referred to.

(1) NaCN + CS$_2$ $\xrightarrow{\text{DMF}}$

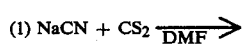

[Ber., 88, 1771 (1955), Ber., 90, 438 (1957)]

(2) 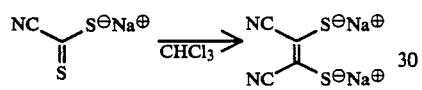

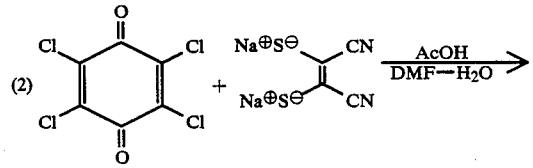

(2)

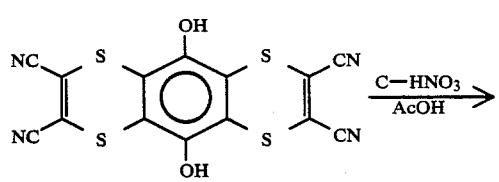

(1)

[Arch. Pharm., 303, 285 (1969)]

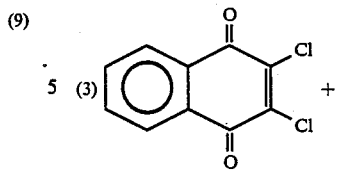  (3)

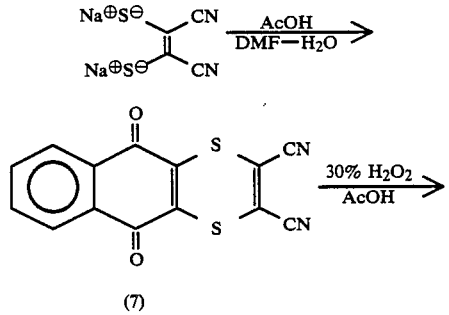

(7)

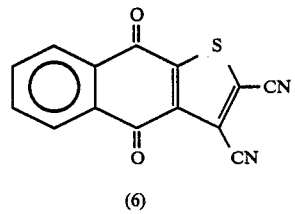

(6)

[E. Merck AG, DAS 1149934 V, 18, 12, 1958]

(4) CH$_2$(CN)$_2$ + CS$_2$ $\xrightarrow[\text{EtOH}]{\text{NaOH}}$ 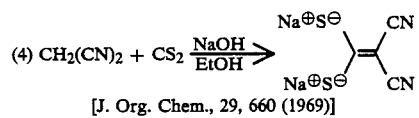

[J. Org. Chem., 29, 660 (1969)]

(5) 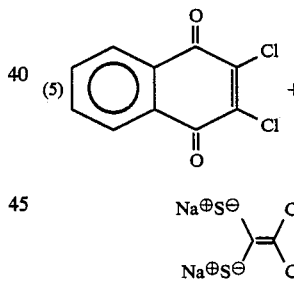

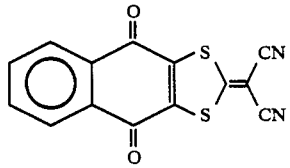

(8)

[Ann., 726 103 (1969)]

(6) 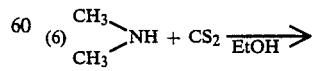

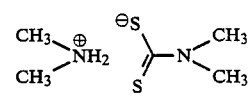

[J. Am. Chem. Soc. 73, 3459 (1951)]

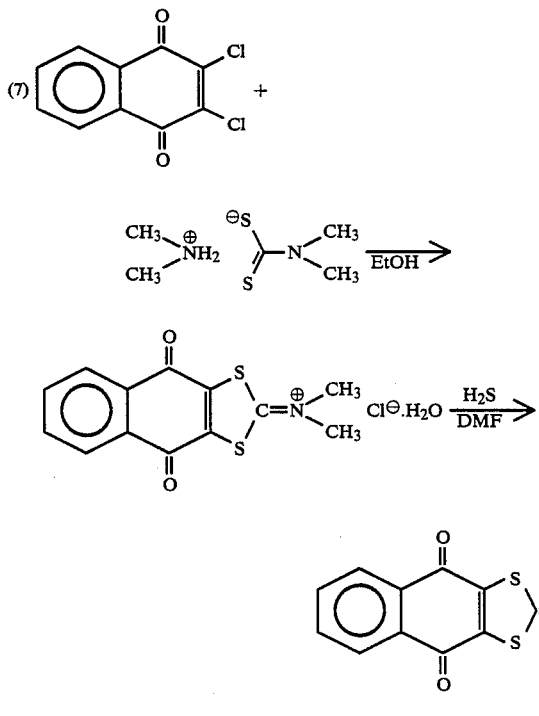

[Tetrahedron Letters 1977, 2203]

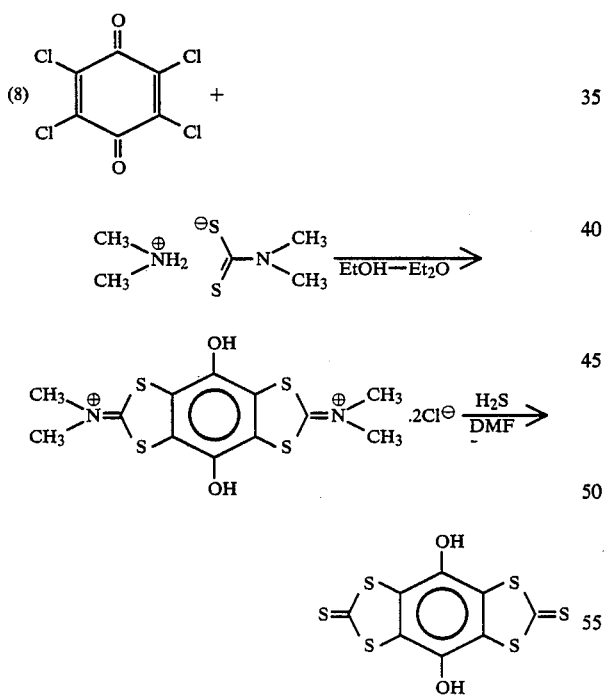

[Tetrahedron Lett., 1977, 2203]

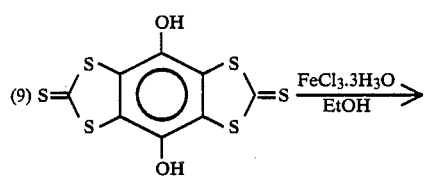

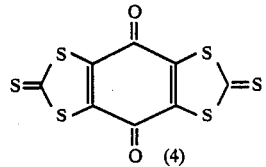

[Chem. Ab st, 88, 623756 (1977)]

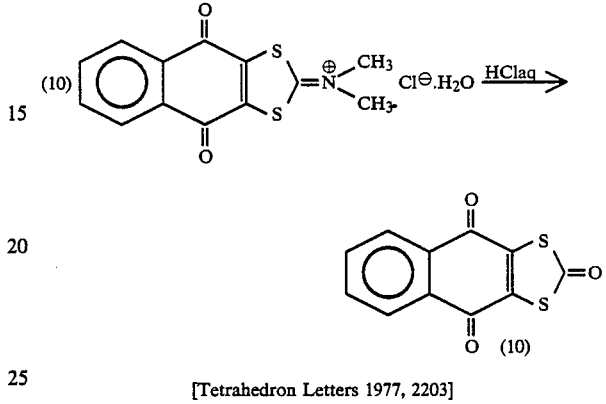

[Tetrahedron Letters 1977, 2203]

In the above schemes, DMF represents dimethylformamide; Ac represents an acetyl group; Et represents an ethyl group; and aq represents an aqueous solution.

Compound (3), a novel compound, can be prepared by oxidizing a hydroquinone derivative represented by the above-described formula (II) with an oxidizing agent.

The starting hydroquinone derivative of formula (II) can be synthesized by reacting a disodium salt prepared from malononitrile [$CH_2(CN)_2$], carbon disulfide, and sodium hydroxide as shown in Reaction Formula 4) above with chloranil in dimethylformamide. The hydroquinone derivative of formula (II) is obtained as a yellowish green crystal having a melting point of 384° C. or higher.

The oxidizing agent to be used includes dicyanodichloro-p-benzoquinone (abbr. as DDQ), $Na_2Cr_2O_7$—$H_2SO_4$, ferric chloride, lead tetraacetate, halide acid salts (e.g., sodium chlorate), oxygen, silver salts (e.g., silver nitrate), etc., with DDQ being particularly preferred.

In general, when DDQ is used as an oxidizing agent, the reaction is carried out in the presence of a solvent, such as dioxane, etc., the reaction mixture is filtered to remove a by-produced dihydroxy compound of DDQ (abbr. as DDHQ), and the desired product is isolated from the filtrate. However, since the starting hydroquinone derivative of formula (II) is slightly insoluble in the solvent, it is preferable to use, as a reaction solvent, tetrahydrofuran in which DDHQ is highly soluble. In this case, the reaction can be effected by dropwise adding a DDQ solution to a tetrahydrofuran solution of the hydroquinone derivative, and the mixture is stirred at room temperature for several hours, followed by filtration to collect the precipitated crystals as a pure product. To the contrary, if in using dioxane as a solvent, the reaction product as obtained contains impurities, such as DDHQ, and should be subjected to a purification procedure.

When ferric chloride is used as an oxidizing agent, the hydroquinone derivative of formula (II) is dissolved in an alcohol that is a good solvent for ferric chloride, and a solution of ferric chloride in an alcohol is added thereto. The mixture is heat-refluxed, followed by allowing to cool. To the reaction mixture is added water, and the thus precipitated crystal is collected by filtration.

The above-described benzoquinone derivatives of formula (I) as produced readily form a charge transfer complex with an electron donor. If desired, they may be converted to their anion or anion radical salts.

Specific examples of the counter cation which can be used in the salts of an anion or anion radical of the benzoquinone derivatives are shown below.

Li$^+$, Na$^+$, K$^+$, Cu$^+$,

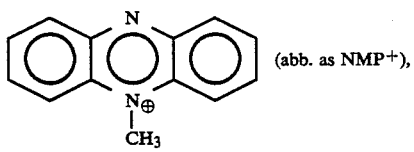
(abb. as NMP$^+$), (CH$_3$)$_4$N$^+$ (abbr. as MeN$^+$), (CH$_3$CH$_2$)$_4$N$^+$ (abbr. as EtN$^+$),

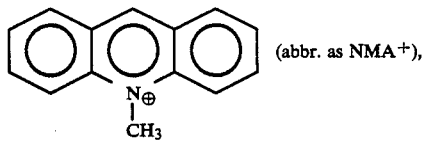
(abbr. as NMA$^+$),

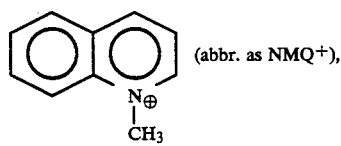
(abbr. as NMQ$^+$),

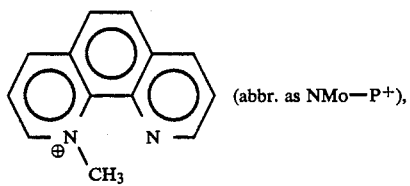
(abbr. as NMo—P$^+$),

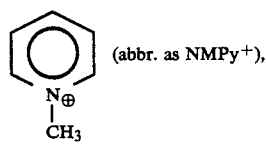
(abbr. as NMPy$^+$),

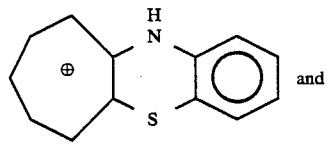
and

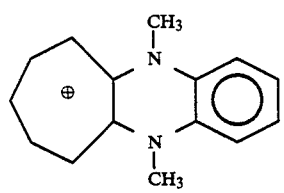

Of these, NMQ$^+$ and NMo-P$^+$ are particularly preferred.

The anion or anion radical salt according to the present invention can be obtained by reacting the benzoquinone derivative of formula (I) with a metal iodide (e.g., lithium iodide) and, if desired, subjecting the product to salt exchange reaction with a cationic compound.

The process for forming the anion or anion radical salt can be illustrated by reactions (i) and (ii) shown below, taking, for instance, a particular case of using lithium iodide.

 (i)

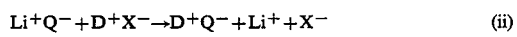 (ii)

wherein Q represents a benzoquinone derivative; D$^+$ represents a cation with which a lithium cation may be exchanged; and X$^-$ represents a counter anion of D$^+$ (e.g., CH$_3$SO$_4^-$).

That is, the benzoquinone derivative of formula (I) is dissolved in an inert organic solvent (e.g., actonitrile) under, if desired, heating. A solution of at least an equimolar amount, and preferably an excess (up to 5 mol per mol of the benzoquinone derivative), of a metal iodide (e.g., LiI, NaI, KI, etc.) in a solvent (preferably the above-recited inert organic solvent) is added to the benzoquinone solution, followed by allowing the mixture to cool to thereby obtain a salt composed of an anion radical of the benzoquinone derivative and an alkali metal cation (e.g., Li$^+$, Na$^+$, K$^+$, etc.) as a counter ion.

If desired, the alkali metal cation may be exchanged with other cation through salt exchange reaction. The salt exchange reaction can be carried out by dissolving the alkali metal cation salt in an inert organic solvent, adding a solution containing an excess of a salt composed of a desired cation, cooling the mixture, and collecting the precipitated crystal by filtration, followed by washing.

The electron donor which can be used as a starting material for producing the charge transfer complex according to the present invention includes aromatic compounds, e.g., benzene, naphthalene, anthracene, pyrene, perylene, etc.; p-phenylenediamine and aromatic condensed compounds derived therefrom; sulfur-containing electron donating compounds, e.g., tetrathiafulvalene (abbr. as TTF), tetrathiatetracene TMTSF), etc.; and the like. In addition, polymers, such as polyvinylcarbazole (abbr. as PVK), may also be used.

Specific examples of these and other electron donors are shown below.

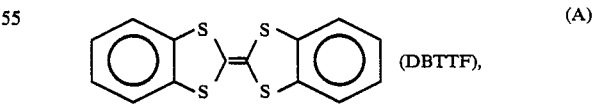 (A)
(DBTTF),

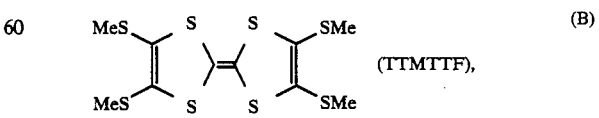 (B)
(TTMTTF),

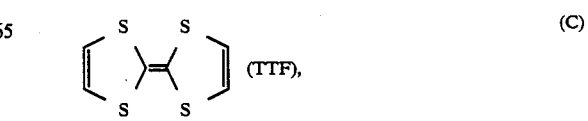 (C)
(TTF),

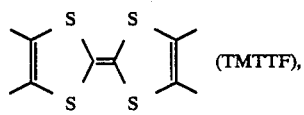 (TMTTF),

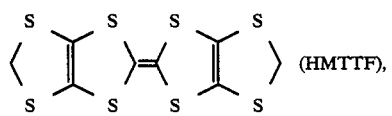 (HMTTF),

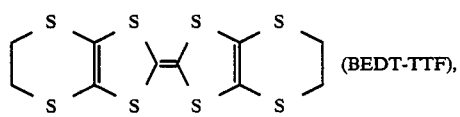 (BEDT-TTF),

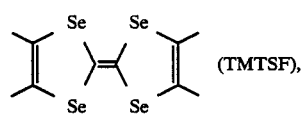 (TMTSF),

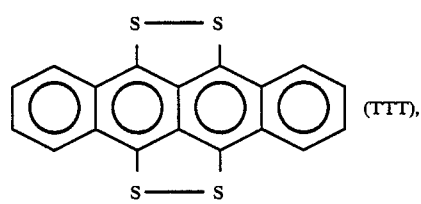 (TTT),

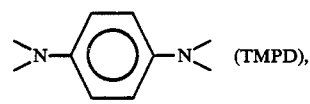 (TMPD),

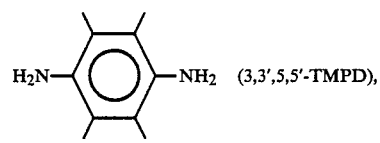 (3,3',5,5'-TMPD),

 (TMB),

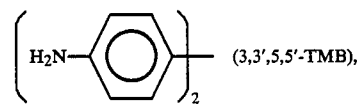 (3,3',5,5'-TMB),

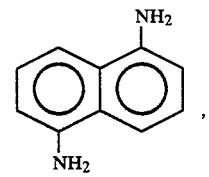,

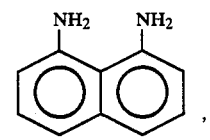,

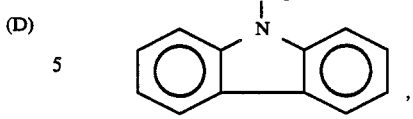 (O)

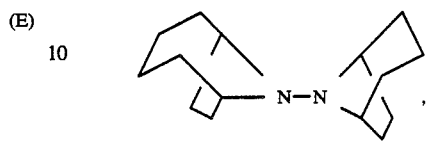 (P)

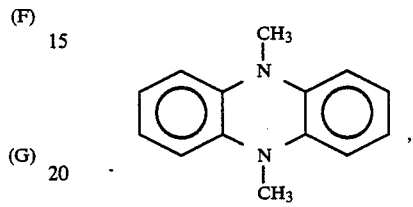 (Q)

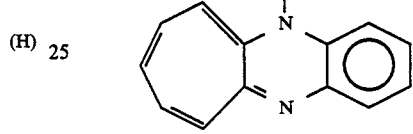 (R)

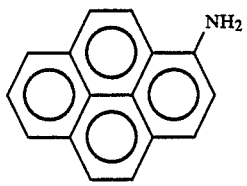 (S)

and

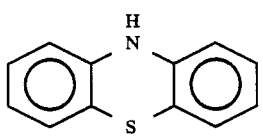 (T)

Of these, TTT and TMTSF are particularly preferred.

The process for producing the charge transfer complex of the present invention includes (1) a process comprising reacting the compound of formula (I) and an electron donating compound in a solvent (e.g., dichloromethane) capable of dissolving both the compound of formula (I) and the electron donating compound and incapable or sparingly capable of dissolving a produced complex to thereby precipitate the produced complex, (2) a process comprising reacting the compound of formula (I) and an electron donating compound in a solvent (e.g., acetonitrile) capable of dissolving both the reactants and a produced complex, and adding a poor solvent (e.g., ether) for the produced complex to thereby precipitate the product, and (3) a process comprising reacting the compound of formula (I) and an electron donating compound in a solvent capable of dissolving both the reactants and a produced complex, and removing the solvent by distillation in the presence or absence of a poor solvent for the produced complex to thereby precipitate the product.

The aforesaid charge transfer complexes formed between the benzoquinone derivatives of formula (I) and an electron donor and salts of an anion or anion radical of the benzoquinone derivatives of formula (I) according to the present invention are useful as organic semiconductors or conductors and applicable to organic electrophotographic materials, condensors, low-resistance heat-sensitive elements, sensors, and the like. For example, in cases where they are utilized as a charge transport material in electrophotographic photoreceptors, they may be mixed with a binder resin, e.g., polycarbonate, polyester, etc., to form a charge transport layer, or may be incorporated into a charge generating layer together with a charge generating material.

The present invention will now be illustrated in greater detail with reference to Synthesis Examples, Reference Examples, and Examples.

SYNTHESIS EXAMPLE 1

(1) Synthesis of Hydroquinone Derivative (II):

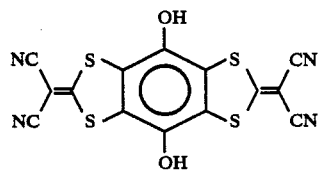

In 180 ml of dimethylformamide was suspended 12.3 g (50 mmol) of chloranil, and the suspension was kept at 10° C. in an ice bath. A solution of 18.4 g (99 mmol) of a disodium salt [(CN)$_2$C$_2$S$_2$Na$_2$] [prepared from malononitrile, carbon disulfide, and sodium hydroxide according to the process described in *J. Org. Chem.*, Vol. 29, 660 (1969)] in 50 ml of water was added dropwise to the chloranil suspension over a period of 30 minutes. After stirring at room temperature for 5 hours, 50 ml of water was added thereto, followed by ice-cooling. The precipitate was collected by filtration, washed with 100 ml of water, and recrystallized from tetrahydrofuran-methanol to obtain 10.09 g (yield: 52%) of the entitled compound as a yellowish green needle-like crystal having a melting point of higher than 384° C. (with decomposition).

IR $\nu^{KBr}$: 1460, 1450 (s), 2210, 1650 (br.), 1360, 1310 (m), 3200, 2930, 1690, 1180, 1100, 670, and 500 cm$^{-1}$.

(2) Synthesis of Compound (3):

In 150 ml of anhydrous tetrahydrofuran was suspended 2.0 g (5.18 mmol) of the hydroquinone derivative as prepared in (1) above, and a solution of 1.41 g (6.22 mmol, 1.2 eq.) of DDQ in 20 ml of anhydrous tetrahydrofuran was added dropwise thereto over a period of 20 minutes. The mixture was stirred at room temperature for 4 hours, followed by filtration to obtain 1.52 g (yield: 76%) of Compound (3) as a purple crystal having a melting point of higher than 397° C. (with decomposition).

IR $\nu_{CN}^{KBr}$: 2203 cm$^{-1}$.

Mass m/e: 384 (M$^+$, 100%).

| Elementary Analysis for C$_{14}$N$_4$S$_4$O$_2$ | | | |
|---|---|---|---|
| Calcd. (%) | C 43.74; | N 14.47; | S 33.36 |
| Found (%) | C 43.74; | N 14.68; | S 33.24 |

SYNTHESIS EXAMPLE 2

In 8 ml of dioxane was suspended 100 mg (0.26 mmol) of the hydroquinone derivative as prepared in Synthesis Example 1-(1), and 70 mg (0.30 mmol) of DDQ was added thereto. The mixture was stirred at room temperature for 4 hours, followed by filtration to obtain 80 mg (crude yield: 80%) of crude Compound (3) as a purple crystal.

SYNTHESIS EXAMPLE 3

In 10 ml of ethanol was suspended 100 mg (0.26 mmol) of the hydroquinone derivative as prepared in Synthesis Example 1-(1), and 140 mg (0.5 mmol, 2 eq.) of FeCl$_3$.6H$_2$O was added thereto. The mixture was heat-refluxed for 10 minutes and then allowed to cool. To the reaction mixture was added 10 ml of water, followed by filtration to obtain 80 mg (yield: 80%) of Compound (3) as a purple crystal.

EXAMPLE 1

Synthesis of Li$^+$(BTDTQ)$^-$ Salt

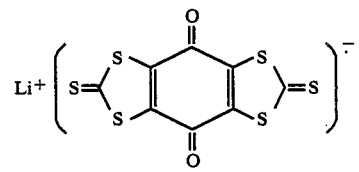

In 40 ml of dry acetonitrile was dissolved 38 mg (0.1 mmol) of BTDTQ (4) under heating, and a solution of 50 mg (0.39 mmol) of LiI in 5 ml of acetonitrile was added thereto. After allowing the mixture to cool, the formed black green needle-like crystals were separated by filtration and washed with acetonitrile to obtain the entitled salt as a blacky green needle-like crystals having a melting point of higher than 355° C. (with decomposition).

| Elementary Analysis for LiC$_8$S$_6$O$_2$.2H$_2$O | | | |
|---|---|---|---|
| Calcd. (%) | C 26.44; | N 1.11; | S 52.93 |
| Found (%) | C 26.98; | N 1.31; | S 50.08 |

EXAMPLE 2

Synthesis of Li$^+$(BDTIQ)$^-$ Salt

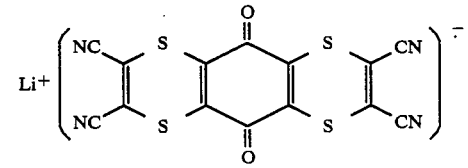

The procedure of Example 1 was followed, except for replacing BTDTQ (4) with BDTIQ (2) to obtain the entitled salt as a bluish purple powder having a melting point of higher than 400° C. (with decomposition).

IR $\nu_{CN}^{KBr}$: 2228 cm$^{-1}$.

| Elementary Analysis for LiC$_{14}$N$_4$S$_4$O$_2$ | | | |
|---|---|---|---|
| Calcd. (%) | C 42.96; | H 0.00; | N 14.32 |
| Found (%) | C 42.17; | H 0.15; | N 14.39 |

EXAMPLE 3

Synthesis of NMA+(BTDTQ)⁻ Salt

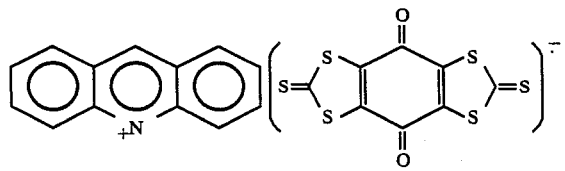

In 20 ml of dry acetonitrile was dissolved 33 mg (0.1 mmol) of the Li+(BTDTQ)⁻ salt as prepared in Example 1 under heating, and a solution of 100 mg (0.33 mmol) of NMA+CH₃SO₄⁻ salt in 5 ml of acetonitrile was added thereto. After allowing the mixture to cool, the precipitated brown crystals were collected by filtration and washed with acetonitrile and diethyl ether to obtain 40 mg of the entitled salt having a melting point of from 230° to 255° C. (with decomposition).

| Elementary Analysis for $C_{22}H_{12}NS_6O_2$ | | | |
|---|---|---|---|
| Calcd. (%) | C 51.34; | H 2.35; | N 2.72 |
| Found (%) | C 50.59; | H 2.22; | N 2.67 |

REFERENCE EXAMPLE 1

Electrical Conductivity of Anion Radical Salt

Specific resistivity ($\rho/\Omega$ cm) of each of the anion radical salts composed of the cation and benzoquinone derivative as shown in Table 1 below in the form of pellets was measured by a two-terminal method as described in R. C. Wheland et al., *J. Am. Chem. Soc.*, 1976, 98, 3916. The results obtained are shown in Table 1.

TABLE 1

| | Logarithm of Specific Resistance ($\rho/\Omega$ cm) | | | |
|---|---|---|---|---|
| | Benzoquinone Derivative | | | |
| Cation | BDT (3) | BDTIQ (2) | BTDTQ (4) | DTPQ (1) |
| Li+ | 6.16 | 7.77 | 4.69 | — |
| EtN+ | 12.0 | 9.56 | 3.94 | — |
| NMPy+ | 11.3 | 4.98 | 4.86 | 6.28 |
| NMo-P+ | 8.45 | 3.58 | 6.65 | 5.86 |
| NMQ+ | 10.6 | 9.91 | 6.48 | — |
| NMA+ | — | — | 7.71 | — |

(Note)
"—": not measured

EXAMPLE 4

Preparation of BDTIQ-DBTTF (1:1) Complex

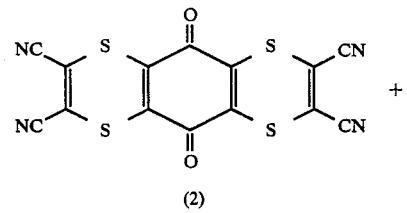

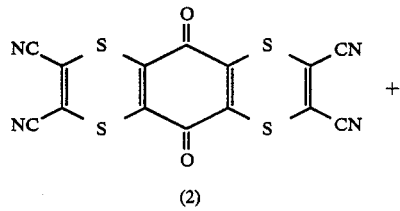

To a boiling solution of 38 mg (0.1 mmol) of Compound (2) in 35 ml of anhydrous methylene chloride was added a boiling solution of 30 mg (0.1 mmol) of Compound (A) in 10 ml of anhydrous methylene chloride, and the mixture was stirred under heating for 5 minutes. After allowing the mixture to cool, the precipitated crystals were separated by filtration to obtain 67 mg of the entitled 1:1 complex as a deep blue crystal having a melting point of from 255° to 258° C. (with decomposition).

IR $\nu_{CN}^{KBr}$: ~2203 cm⁻¹.

| Elementary Analysis for $C_{28}H_8N_4S_8O_2$ | | | |
|---|---|---|---|
| Calcd. (%) | C 48.82; | H 1.17; | N 8.13 |
| Found (%) | C 48.36; | H 0.96; | N 7.98 |

EXAMPLE 5

Preparation of BDTIQ-TTMTTF (1:1) Complex

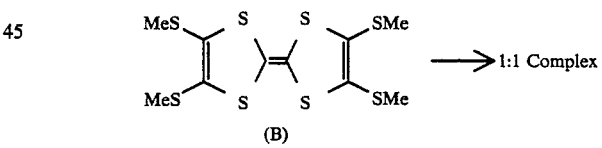

To a boiling solution of 25 mg (0.07 mmol) of Compound (2) in 20 ml of anhydrous methylene chloride was added 25 mg (0.07 mmol) of Compound (B), and the mixture was stirred while heating until a black precipitate began to appear. The reaction mixture was allowed to cool and filtered to obtain 49 mg of the entitled 1:1 complex as a black solid having a melting point of from 184° to 186° C. (with decomposition).

IR $\nu_{CN}^{KBr}$: 2207 cm⁻¹.

| Elementary Analysis for $C_{24}H_{12}N_4S_{12}$ | | | |
|---|---|---|---|
| Calcd. (%) | C 37.28; | H 1.56; | N 7.25 |
| Found (%) | C 37.13; | H 1.25; | N 8.07 |

EXAMPLE 6

Preparation of BDTQ-TMTSF (1:1) Complex

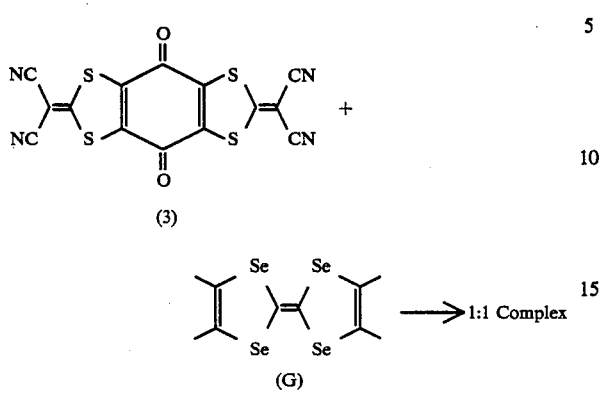

To a boiling solution of 29 mg (0.08 mmol) of Compound (3) in 30 ml of anhydrous methylene chloride was added a boiling solution of 34 mg (0.08 mmol) of Compound (G) in 25 ml of anhydrous methylene chloride. The mixture was stirred for 5 minutes while heating to obtain 61 mg of the entitled 1:1 complex as a black precipitate having a melting point of from 220° to 230° C. (with decomposition).

IR $\nu_{CN}^{KBr}$: 2202 cm$^{-1}$.

| Elementary Analysis for $C_{24}H_{12}N_4S_4Se_4O_2$ | | | |
|---|---|---|---|
| Calcd. (%) | C 34.63; | H 1.45; | N 6.73 |
| Found (%) | C 35.10; | H 1.30; | N 7.07 |

EXAMPLE 7

Preparation of EDTQ-TMTSF (1:1) Complex

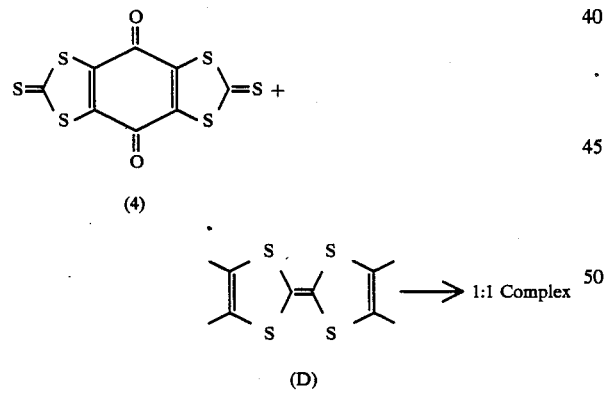

To a boiling solution of 32 mg (0.1 mmol) of Compound (4) in 15 ml of methylene chloride was added a boiling solution of 26 mg (0.1 mmol) of Compound (D) in 5 ml of methylene chloride. The reaction mixture was allowed to cool to obtain 55 mg of the entitled 1:1 complex as a greenish gray precipitate having a melting point of 258° C. or higher (with decomposition).

| Elementary Analysis for $C_{18}H_{12}O_2S_{10}$ | | |
|---|---|---|
| Calcd. (%) | C 37.22; | H 2.08 |
| Found (%) | C 37.04; | H 2.09 |

EXAMPLE 8

Preparation of BTDTQ-TTT (1:1) Complex

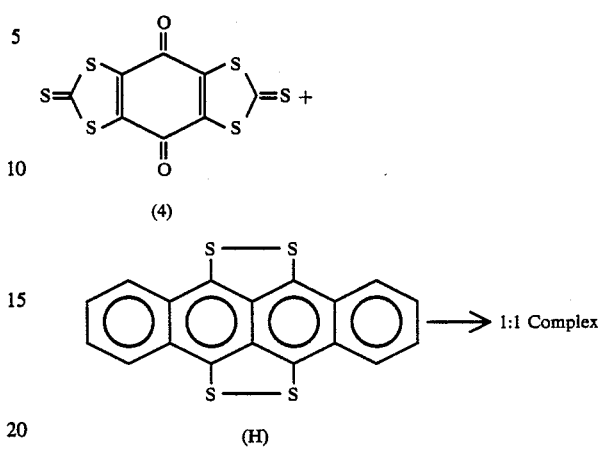

In 40 ml of methylene chloride was dissolved 32 mg (0.1 mmol) of Compound (4), and 35 mg (0.1 mmol) of Compound (H) was extracted with the resulting solution in a Soxhlet's extractor for 24 hours. After allowing the extract to cool, there was obtained 40 mg of the entitled 1:1 complex as a black precipitate having a melting point of 400° C. or higher (with decomposition).

| Elementary Analysis for $C_{26}H_8O_2S_{10}$ | | |
|---|---|---|
| Calcd. (%) | C 46.40; | H 1.20 |
| Found (%) | C 47.52; | H 1.46 |

EXAMPLE 9

Preparation of DTPQ-TTT (1:1) Complex

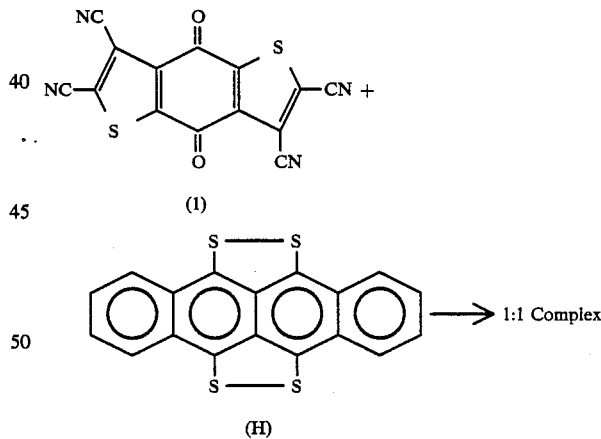

In 250 ml of methylene chloride was suspended 32 mg (0.1 mmol) of Compound (1), and 35 mg (0.1 mmol) of Compound (H) was extracted with the resulting solution in a Soxhlet's extractor for 24 hours. The extract was concentrated to a volume of 50 ml to obtain 50 mg of the entitled 1:1 complex as brown precipitate having a melting point of 400° C. or higher.

REFERENCE EXAMPLE 2

Electrical Conductivity of Charge Transfer Complex

Specific resistivity ($\rho/\Omega$ cm) of each of the charge transfer complexes in the form of pellets composed of the donor and acceptor as shown in Table 2 below was measured by the two-terminal method as in Reference Example 1. The results obtained are shown in Table 2.

TABLE 2

| Doner | Acceptor (3) | (2) | (4) | (1) |
|---|---|---|---|---|
| (I) | — | — | 11.11 | 7.20 |
| (H) | 2.64 | 5.40 | 1.00 | — |
| (D) | 3.54 | 4.07 | 1.76 | 5.51 |
| (R) | 9.40 | 10.28 | 4.57 | 6.00 |
| (C) | 4.11 | 3.86 | 4.85 | 3.23 |
| (G) | 0.05 | — | — | — |

TABLE 2-continued

| Doner | Acceptor (3) | (2) | (4) | (1) |
|---|---|---|---|---|
| (F) | 3.11 | 3.67 | 4.32 | — |
| (E) | 3.01 | 3.85 | 3.34 | — |
| (B) | 1.30 | 0.99 | 5.65 | — |
| (A) | 4.61 | 1.02 | 6.49 | — |
| (T) | — | 7.71 | — | — |

(note) "—": not measured

While the invention has been described in detail and with reference to specific embodiments thereof, it will be apparent to one skilled in the art that various changes and modifications can be made therein without departing from the spirit and scope thereof.

What is claimed is:

1. A charge transfer complex formed between a benzoquinone derivative represented by formula (I)

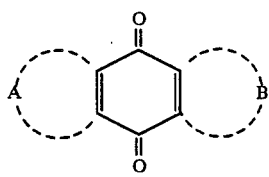 (I)

wherein one of

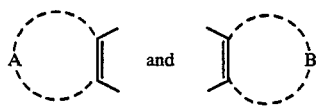

represents a heterocyclic ring selected from the group consisting of

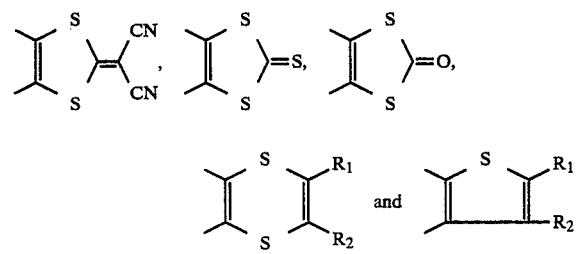

and the other represents one of said heterocyclic rings or a group of formula

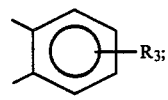

$R_1$, $R_2$, and $R_3$ each represents a hydrogen atom, an alkyl group, an aryl group, an aralkyl group, an alkoxy group, a halogen atom, a nitro group, a cyano group, or a carboxylic ester group, and an electron donor.

2. A process for producing a charge transfer complex formed between a brenzoquinone derivative represented by formula (I)

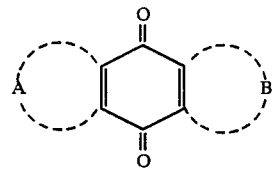 (I)

wherein one of

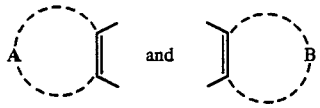

represents a heterocyclic ring selected from the group consisting of

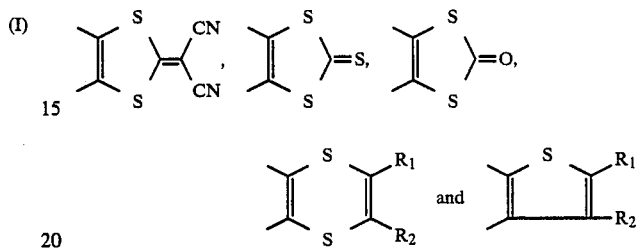

and the other represents one of said heterocyclic ring or a group of formula

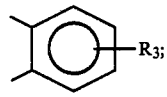

$R_1$, $R_2$, and $R_3$ each represents a hydrogen atom, an alkyl group, an aryl group, an aralkyl group, an alkoxy group, a halogen atom, a nitro group, a cyano group, or a carboxylic ester group, and an electron donor, which comprises reacting the benzoquinone derivative and the electron donor in a solvent capable of dissolving both the benzoquinone derivative and the electron donor and incapable or sparingly capable of dissolving a produced complex to thereby precipitate the produced complex.

3. A process for producing a charge transfer complex formed between a benzoquinone derivative represented by formula (I)

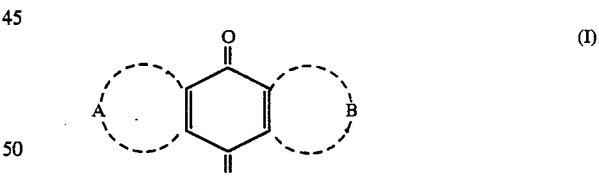 (I)

wherein one of

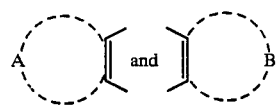

and represents a heterocyclic ring selected from the group consisting of

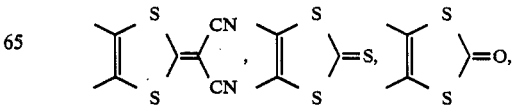

-continued

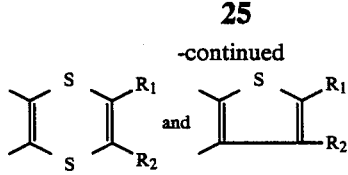

and the other represents one of said heterocyclic ring or a group of formula

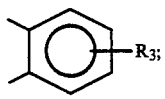

$R_1$, $R_2$, and $R_3$ each represents a hydrogen atom, an alkyl group, an aryl group, an aralkyl group, an alkoxy group, a halogen atom, a nitro group, a cyano group, or a carboxylic ester group, and an electron donor, which comprises reacting the benzoquinone derivative and the electron donor in a solvent capable of dissolving both the reactants and a produced complex, and adding a poor solvent for the produced complex to thereby precipitate the product.

4. A process for producing a charge transfer complex formed between a benzoquinone derivative represented by formula (I)

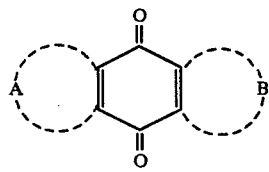 (I)

wherein one of

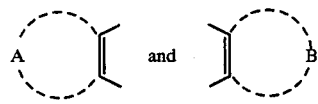

represents a heterocyclic ring selected from the group consisting of

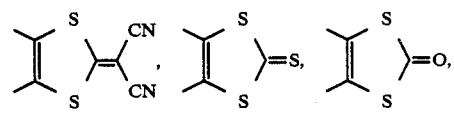

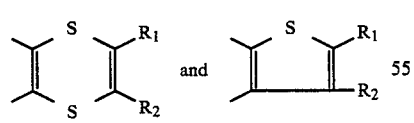

and the other represents one of said heterocyclic ring or a group of formula

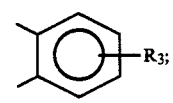

$R_1$, $R_2$, and $R_3$ each represents a hydrogen atom, an alkyl group, an aryl group, an aralkyl group, an alkoxy group, a halogen atom, a nitro group, a cyano group, or a carboxylic ester group, and an electron donor, which comprises reacting the benzoquinone derivative and the electron donor in a solvent capable of dissolving both the reactants and a produced complex, and removing the solvent by distillation in the presence or absence of a poor solvent for the produced complex to thereby precipitate the product.

5. A charge transfer complex as claimed in claim 1, wherein said electron donor is a material selected from the group consisting of aromatic compounds, p-phenylenediamine and aromatic condensed derivatives thereof, sulfur-containing electron donating compounds, and polymers.

6. A charge transfer complex as claimed in claim 1, wherein said electron donor is a compound selected from the group consisting of:

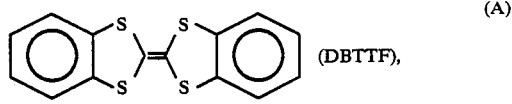 (A)

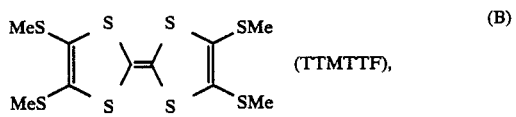 (B)

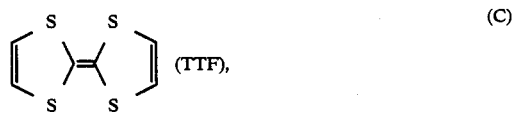 (C)

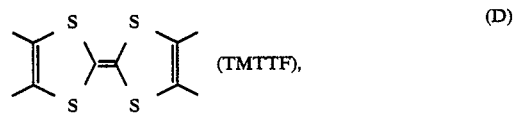 (D)

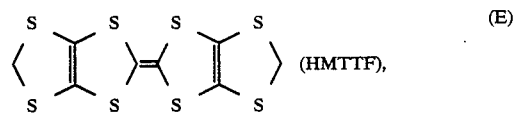 (E)

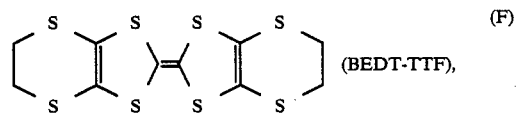 (F)

 (G)

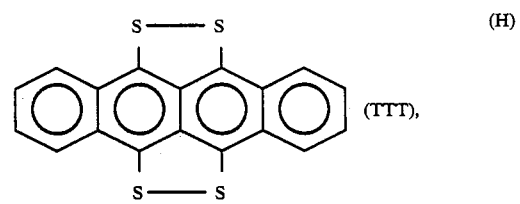 (H)

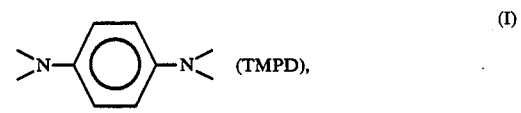 (I)

-continued

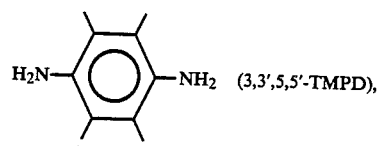 (3,3',5,5'-TMPD),

 (TMB),

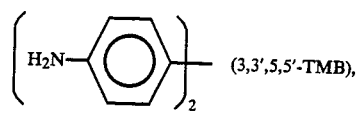 (3,3',5,5'-TMB),

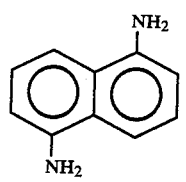

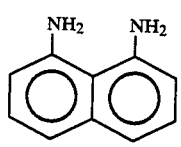

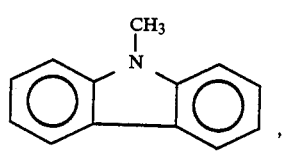

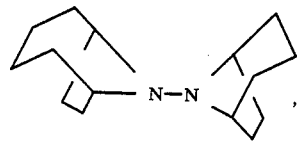

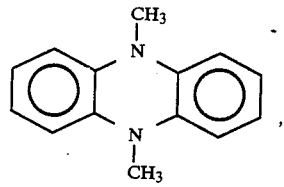

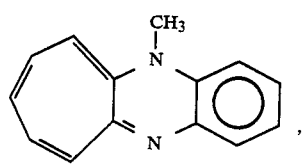

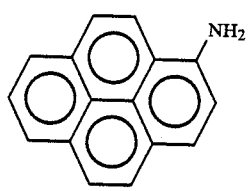

and (J) 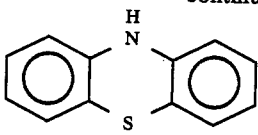 (T)

7. A Charge transfer complex as claimed in claim 1, wherein said electron donor is selected from the group consisting of benzene, naphthalene, anthracene, pyrene, perylene, p-phenylenediamine, tetrathiafulvalene, tetrathiatetracene, tetramethyltetraselenafulvalene, and polyvinylcarbazole.

8. A charge transfer complex as claimed in claim 1, wherein said electron donor is selected from the following group of compounds:

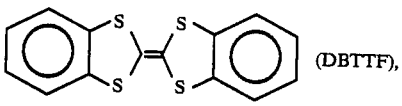 (DBTTF), (A)

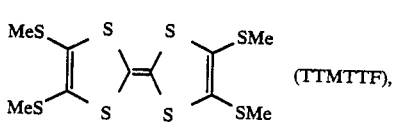 (TTMTTF), (B)

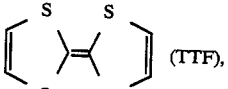 (TTF), (C)

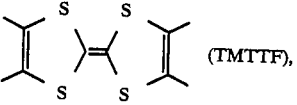 (TMTTF), (D)

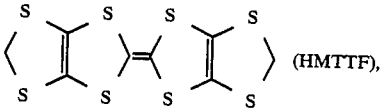 (HMTTF), (E)

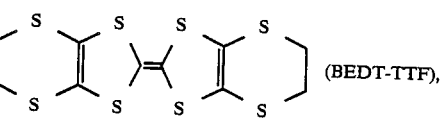 (BEDT-TTF), (F)

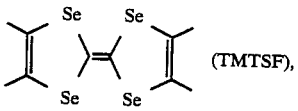 (TMTSF), (G)

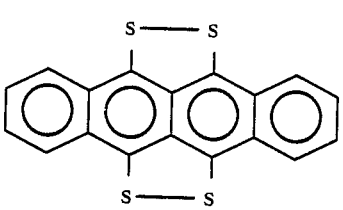 (TTT), (H)

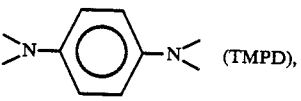 (TMPD), (I)

-continued
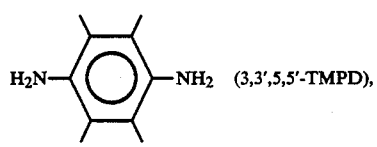 (3,3',5,5'-TMPD),
 (TMB),
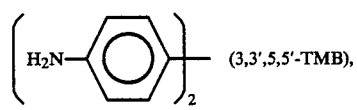 (3,3',5,5'-TMB),
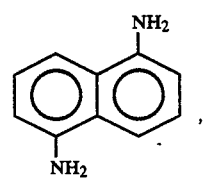,
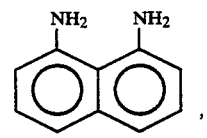,
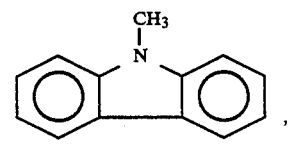,
-continued
 (P)
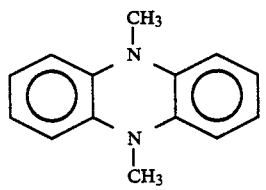 (Q)
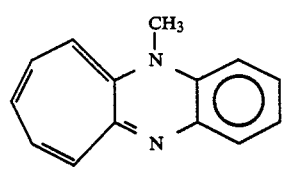 (R)
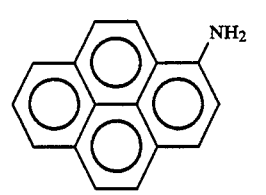 (S)
and
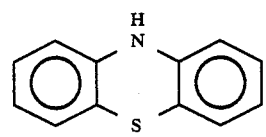 (T)
9. A charge transfer complex as claimed in claim 1, wherein said electron donor is selected from tetrathiatetracene and tetramethyltetraselenafulvalene.
* * * * *